(12) United States Patent
Nijhof et al.

(10) Patent No.: US 8,348,507 B2
(45) Date of Patent: Jan. 8, 2013

(54) OBJECT LOCALIZATION IN X-RAY IMAGES

(75) Inventors: Niels Nijhof, Eindhoven (NL); Herman Stegehuis, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 190 days.

(21) Appl. No.: 12/933,915

(22) PCT Filed: Mar. 20, 2009

(86) PCT No.: PCT/IB2009/051175
§ 371 (c)(1),
(2), (4) Date: Sep. 22, 2010

(87) PCT Pub. No.: WO2009/118671
PCT Pub. Date: Oct. 1, 2009

(65) Prior Publication Data
US 2011/0026666 A1   Feb. 3, 2011

(30) Foreign Application Priority Data
Mar. 28, 2008  (EP) .................................... 08153526

(51) Int. Cl.
*H05G 1/02* (2006.01)
(52) U.S. Cl. .......................................... 378/197; 378/62
(58) Field of Classification Search .............. 378/62, 378/205, 193, 196, 197, 55
See application file for complete search history.

(56) References Cited

U.S. PATENT DOCUMENTS

| | | | |
|---|---|---|---|
| 6,298,110 B1 | 10/2001 | Ning | |
| 6,704,392 B2 | 3/2004 | Ebben et al. | |
| 7,177,389 B2 | 2/2007 | Gary | |
| 7,978,817 B2 * | 7/2011 | Rietzel | 378/65 |
| 2002/0141540 A1 * | 10/2002 | Vaillant et al. | 378/197 |
| 2004/0066880 A1 | 4/2004 | Oikawa | |
| 2005/0100126 A1 | 5/2005 | Mistretta et al. | |
| 2008/0049896 A1 * | 2/2008 | Kuduvalli | 378/65 |

FOREIGN PATENT DOCUMENTS

| | | |
|---|---|---|
| WO | 9714359 A1 | 4/1997 |
| WO | 2007046036 A1 | 4/2007 |

OTHER PUBLICATIONS

Kottkamp et al: "Electromagnetic Versus Fluoroscopic Mapping of the Inferior Isthmus for Ablation of Typical Atrial Flutter: A Prospective Randomized Study"; Circulation: Journal of the American Heart Association. 2000, vol. 102, pp. 2082-2086.

* cited by examiner

Primary Examiner — Hoon Song

(57) ABSTRACT

An x-ray system (100) comprises a gantry (102) on which an x-ray source (104) and an x-ray detector (106) are mounted. A control unit (110) comprises means (114) for effectuating a wiggling motion of the gantry, wherein an axis (116) connecting the x-ray source and the x-ray detector traces a surface (128) of a cone (118). The x-ray source and the x-ray detector have a fixed position with respect to the axis. The control unit comprises means (120) for acquiring a series of x-ray images during the wiggling motion of the gantry. An object recognition unit (122) detects an object (124) appearing in the series of x-ray images to obtain a tracked path. A depth estimation unit (126) uses the tracked path for estimating a depth parameter indicative of a position of the object in a direction substantially parallel to the axis (116).

15 Claims, 7 Drawing Sheets

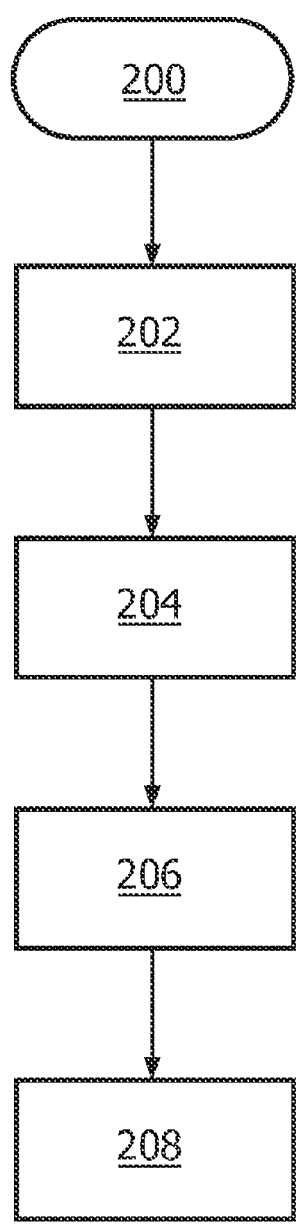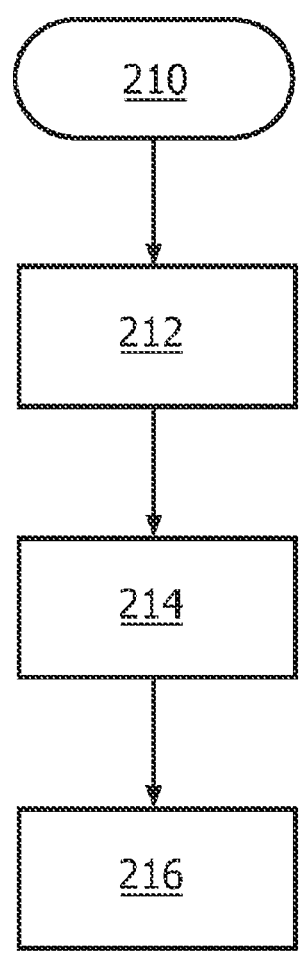
FIG. 2A
FIG. 2B

OBJECT LOCALIZATION IN X-RAY IMAGES

FIELD OF THE INVENTION

The invention relates to object localization in x-ray images.

BACKGROUND OF THE INVENTION

X-ray fluoroscopy is often used for guiding electrophysiology (EP) ablation procedures. It shows the position of all catheters in real-time. 3D mapping has greatly helped the development of complex ablation procedures by showing the position of the catheter in relation to a 3D representation of the cardiac contours. However, neither tool can show the position of all catheters in relation to each other or the detailed endocardial anatomy, in real time.

The EP Navigator, which is available from Philips Healthcare, is able to confirm the position of a catheter or lead position with respect to a 2D projection of a detailed 3D cardiac anatomy in the EP intervention lab. This information can help a physician to carry out complex EP procedures with greater confidence, in a more intuitive way. Such tools may provide an automatically segmented 3D CT image. This image of the patient's cardiac anatomy is combined with live fluoroscopy data to show the exact position of all catheters. EP navigator enables a user to select a 3D anatomy (for example, left atrium and pulmonary veins) to be combined with the live fluoroscopic images. The resulting composite image provides an accurate indication of the position of all catheters in relation to the 2D projection of the detailed 3D anatomy of the heart.

Due to the complexity of the anatomy and the lack of integrated tools, complex ablation procedures are very time-consuming and usually last several hours. Success of the procedure depends on accuracy of the positioning of the catheter. Maintaining good contact between tissue and the catheter tip is important.

An electromagnetic mapping system is described in "Electromagnetic Versus Fluoroscopic Mapping of the Inferior Isthmus for Ablation of Typical Atrial Flutter" by Hans Kottkamp, M D et al., in Circulation, 2000, 102:2082-2086 (hereinafter: Kottkamp et al.). This electromagnetic mapping system consists of an external, ultralow emitter of a magnetic field, a set of 2 catheters with miniature magnetic field sensors, and a processing computer unit. Under certain circumstances described in Kottkamp et al., this electromagnetic mapping system allows to perform a mapping procedure using the electromagnetic mapping system without continuous fluoroscopy, while using additional x-ray projections, like the right anterior oblique view, if necessary.

SUMMARY OF THE INVENTION

It would be advantageous to have an improved object localization system. To better address this concern, in a first aspect of the invention a system is presented that comprises a gantry on which an x-ray source and an x-ray detector are mounted;

at least one motor for rotating the gantry;

a control unit for controlling the x-ray source and the x-ray detector to acquire x-ray images and for driving the motor to control a movement of the gantry, wherein the control unit comprises means for effectuating a wiggling motion of the gantry, wherein an axis connecting the x-ray source and the x-ray detector traces a surface of a cone, wherein the x-ray source and the x-ray detector have a fixed position with respect to the axis, wherein the control unit comprises means for acquiring a series of x-ray images during the wiggling motion of the gantry;

an object recognition unit for detecting and tracking an object appearing in the series of x-ray images to obtain a tracked path, wherein the tracked path represents a plurality of positions at which the object was detected in the series of images; and a depth estimation unit for using the tracked path for estimating a depth parameter indicative of a position of the object in a direction substantially parallel to the axis.

This makes it possible to obtain a depth estimate without using special localization hardware, because the x-ray system, which is already in use during an intervention, is used to obtain the depth estimate of the object. The system is convenient to use, because it does not involve large rotational movements of the gantry or time-consuming positioning procedures. An advantage is that it is no longer necessary to use an electromagnetic EP navigation system.

The x-ray images, by themselves, provide information about two dimensions of the position of the object. The third dimension, in particular along the axis intersecting the x-ray source and the middle of the detector plane, cannot normally be derived by inspecting the x-ray images. This third dimension is referred to as the depth of the object. The wiggling motion of the gantry causes the x-ray source and x-ray detector to wiggle, which provides views of slightly different perspectives. The slightly different perspectives may be used to estimate the depth parameter of the object. Because a plurality of images is acquired along the wiggling motion, the accuracy of the depth estimate is improved compared to stereo computations based on only two images. Moreover, the wiggling motion is not hindered by objects that may be positioned near the patient because the wiggling motion only spans a relatively small angular range.

The wiggling motion is usually limited to at most about 10 degrees, at maximum to about 15 degrees, which prevents the system to hinder most objects surrounding the patient. Another characteristic of the wiggling motion is that it may be a substantially periodic motion or even a fully periodic motion. The same trajectory may be repeated a number of times to improve the accuracy of the depth estimation. As long as the base of the cone is smooth (e.g., circular or elliptic), it is relatively easy to perform the wiggling motion repeatedly in a smooth movement, which leads to a more stable, reproducible movement.

The tracked path may be compared to the base of the cone. Typically the tracked path has a shape similar to the base of the cone or symmetric to the shape of the base. However, depending on the depth of the object, the shape of the tracked path will be larger or smaller. This property may be used to establish the depth parameter of the position of the object.

The system is highly suitable for electrophysiological ablation procedures, in which the depth of the tip or electrode(s) of an ablation catheter is established by the x-ray system. More generally, the system may be applied to estimate the depth of a part of a catheter, for example the catheter tip. The system may be used during a percutaneous intervention, for example to provide three-dimensional localization of a needle tip or an instrument position.

The three-dimensional position of the object (taking into account the depth parameter and the location of the object in at least one x-ray image, may be indicated in a predetermined three-dimensional anatomic image, for example a CT or MRI image or a surface cardiac model.

Further aspects of the invention are defined in the independent claims. The dependent claims define advantageous embodiments.

BRIEF DESCRIPTION OF THE DRAWINGS

These and other aspects of the invention will be further elucidated and described with reference to the drawing, in which

FIGS. 2A and 2B are flowcharts illustrating processing steps;

DETAILED DESCRIPTION OF EMBODIMENTS

In this detailed description, several methods, systems, and computer program products are described that enable to estimate image depth information by use of conventional X-ray imaging. One of the applications discussed is three-dimensional (3D) position localization for electrophysiology (EP) procedures. However, the ideas and the embodiments described are applicable to a wide range of applications, in particular where automated object detection and tracking is feasible.

Such X-ray based 3D localization may be based on (ultra) low-dose fluoroscopy on monoplane geometry. Biplane and other geometries may also be used, although the information of only one detector is sufficient to provide depth information. The methods may be based in part on automated object tracking and/or signal processing, and on precession of the gantry on which the X-ray source and/or X-ray detector are mounted.

Fluoroscopy guided ablation focuses on guiding the physician through the position of the EP catheters relative to the heart (and relative to each other) for focal ablation. The ablation may take place during an intervention involving atrial fibrillation (AF). Since catheter guidance is anatomy related and, therefore, rather complex and time consuming, utilities that assist in navigation, planning and mapping are considered essential tools in the modern EP lab.

Fluoroscopy based depth estimation enables (semi) real-time 3D navigation and mapping with standard EP catheters, seamlessly integrated in the X-ray system. X-ray based depth estimation tools may reduce or remove the need for dedicated localization tools and hardware. Such dedicated localization tools and hardware may for example be based on magnetic measurements. These dedicated localization tools are typically used in addition to the X-ray system, wherein the X-ray system may be used for visualization of anatomic tissues as well as interventional tools, whereas the localization tools are used to establish the position of one or more interventional tools. Due to their separate acquisition mode, special processing is required to register the position information to the imaging information.

An approach to real-time X-ray based depth estimation is by 'wiggling' the geometry in a cone-style motion trajectory (precession).

Figure 1:
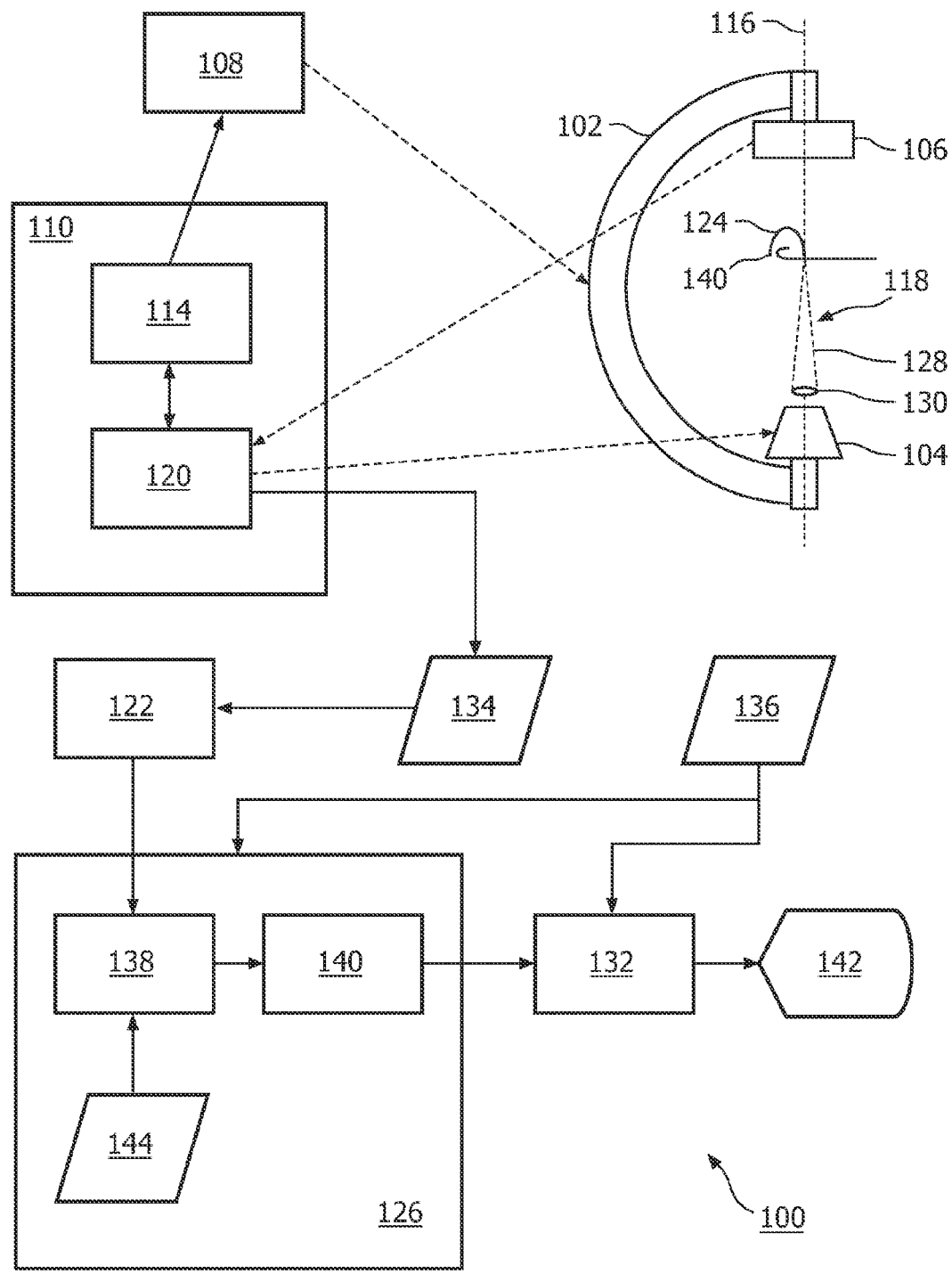
FIG. 1 is a diagram of an embodiment.

FIG. 1 illustrates a simplified block diagram of an x-ray system 100 which may be used to determine a depth parameter of an object. The figure shows only those components that are needed to explain the concepts disclosed in this description. An actual x-ray system may comprise many more components which are not discussed in this document. The x-ray system 100 comprises a gantry 102. The gantry is mounted on a suspension (not shown) and may be rotated about one or more axes of rotation. Usually, the gantry is rotatable around two or more orthogonal axes of rotation. This rotation is effectuated by one or more motors 108 (for example, one motor for each axis of rotation). The x-ray source 104 and x-ray detector 106 are mounted on the gantry 102. The x-ray source 104 may be an x-ray tube known in the art. The x-ray detector may comprise an image intensifier or a flat panel detector known in the art.

The x-ray system further comprises a control unit 110 for controlling the at least one motor 108, the x-ray source 104, and the x-ray detector 106. The control unit 110 is arranged to operate in response to user input. For example, a joy-stick like control may be provided to enable a user to rotate the gantry around two axes of rotation. Also, a pedal may be provided; when the pedal is depressed, one or more x-ray images are acquired. The control unit may take care of this. To acquire an image, the control unit 110 may trigger the x-ray source 104 to produce an x-ray pulse. Thereupon, the x-ray detector 106 may send the resulting x-ray projection image back to the control unit 120, which stores it in a memory location 134.

An imaginary axis 116 intersects the x-ray source 104 and the x-ray detector 106. During the wiggle of the gantry, the imaginary axis 116 is fixed with respect to the x-ray source 104 and the x-ray detector 106. Consequently, when the gantry moves (rotates, wiggles), the imaginary axis moves (rotates, wiggles) along with the gantry. The control unit 110 comprises means 114 for effectuating a wiggling motion of the gantry by means of the motor 108. The wiggling motion is such that the axis 116 connecting the x-ray source and the x-ray detector traces a surface 128 of an imaginary cone 118. The control unit also comprises means 120 for acquiring a series of x-ray images during the wiggling motion of the gantry. The means 114 and 120 may be arranged to operate in response to a user input. For example, a dedicated button may be provided. Pressing the button may start the wiggling motion and series acquisition. Releasing the button may stop the wiggling motion and series acquisition. Alternatively, the wiggling motion and series acquisition stop may automatically, after a predetermined time.

The imaginary cone 118 has its apex 140 at the isocenter of the rotation, wherein the isocenter is a point that the axis 116 always intersects, regardless of the rotational movement of the gantry 102. The base 130 of the cone 118 may in general have any planar shape. Preferably it is a closed curve, and preferably it is a smooth curve. A closed curve has the advantage that it is easy to make the movement periodic. A smooth curve has the advantage that it is easier to control the movement and makes the measurement more stable and less noisy. Alternatively the base of the curve forms a linear shape, in which case the gantry may move linearly (and preferably repeatedly) between two end positions.

Typically, during the wiggling motion and simultaneous image acquisition, an object 124 to be tracked is kept in the field of view of the detector 106. This object becomes visible in the x-ray images. Preferably, the object comprises a suitable material that can be distinguished from the surrounding tissue material. For example, the object comprises a material with a high x-ray attenuation coefficient (e.g., a metal). The object can be an electrode mounted on a catheter. The tip of the catheter can also be the object to be tracked.

An object recognition unit 122 is provided for detecting and tracking an object 124 appearing in the series of x-ray images to obtain a tracked path. Any known method can be used to detect the object in the x-ray image. For example, a blob detection algorithm can be used to detect a small metal object such as an electrode. Also, algorithms to detect the tip of a catheter are known in the art. The tracked path is obtained by the sequential positions of the object in the series of x-ray images. The tracked path may comprise an unordered set of coordinates. However, the tracked path may also be an ordered sequence of coordinates. Such an ordered sequence contains more information, which may be used to obtain better results in the depth estimation unit.

A depth estimation unit 126 is provided. The depth estimation unit uses the tracked path to estimate the depth parameter. For example, the change of the x-coordinate or the change of the y-coordinate of the object in the x-ray images may be used to estimate the depth. The larger these deviations, the further away the object is from the isocenter. The direction of the change may be used as an indication at which side of the isocenter the object is located. An example of computations involved in the estimation of the depth parameter is provided elsewhere in this description. In general, the depth may be estimated by comparing the tracked path with the base 130 of the cone, because the tracked path may resemble a scaled version of the base, wherein the scale depends on the distance of the object from the isocenter.

Information available in a dataset 136 representing a three-dimensional anatomical image which corresponds to the patient being imaged, may be used to improve the accuracy of the depth information. For example, in some electrophysiology applications it may be assumed that the object (e.g. a catheter tip) is at the boundary of (or more generally, inside) a segmented volume of the dataset 136, for example an atrium.

Preferably, the wiggling motion is not too large. For example, the wiggling motion spans an angle of at most about 10 degrees, wherein the angle is measured with respect to the axis. Alternatively, a displacement of the x-ray source during the wiggling motion is not greater than a dimension of the x-ray detector. For example, if the dimension of the x-ray detector is 20×30 cm, the displacement of the x-ray source during the wiggling motion is also not more than 20×30 cm.

The wiggling motion is preferably a periodic motion. This is advantageous for the signal processing relating to the depth estimation, because it helps to filter out noise signals, especially if the period of the periodic motion is different from any periodicity of the noise signals. For example, if the object moves due to cardiac motion or respiratory motion, the disturbances of the object location may be filtered out by the periodic wiggling motion.

The cone may have a circular base or an elliptical base. This means that the wiggling motion is circular or elliptical, which are smooth motions. A circular base has the advantage that every determined object location contributes equally to the accuracy of the depth estimation. This can be understood by realizing that when the base is a circle, the tracked path is also a circle. Each object location helps equally in estimating the radius of the tracked path, and the depth estimation may be based on the radius of the tracked path. Alternatively, the cone may have a linearly shaped base, for example a linear movement from position A to position B, followed by a linear movement back to A. Such a linear movement is relatively easy to implement in an x-ray system. Such a linearly shaped base may also be regarded elliptical, since it constitutes an ellipse in which the shortest axis has zero length. A nonlinear elliptical base has the advantage that more comprehensive information is gathered from more different perspectives, which makes the depth estimation more accurate.

The depth estimation unit 126 may comprise means 138 for comparing a base of the cone with the tracked path, thereby obtaining a scale of the tracked path. The base of the cone 144 may be stored digitally in a memory of the depth estimation unit 126. The depth estimation unit 126 may further comprise means 140 for estimating the depth parameter based on the scale of the tracked path. The base of the cone may comprise a circle. In this case, the tracked path also defines a circle, and the scale of the tracked path is based on a radius of the circle defined by the tracked path.

Although any kind of object may be localized, the system is especially suitable for detecting an object comprising at least a tip or an electrode of an electrophysiology ablation catheter. Depth estimation is of great importance in ablation procedures, and the x-ray based depth estimation removes the need for a separate electromagnetic localization system. However, the system may be used during any kind of percutaneous intervention. Other applications are also envisaged.

A graphical unit 132 is preferably provided for indicating a position of the object with respect to a three-dimensional anatomical image represented by a dataset 136. This indication is based on the three-dimensional position of the object, including the depth parameter. The graphical unit 132 determines the position of the object relative to the three-dimensional anatomical image represented by the dataset 136. The three-dimensional position of the object may be computed by considering the depth parameter in combination with the position of the object in an x-ray image, for example one of the x-ray images in the series acquired during the wiggling motion. Instead of using only the position of the object in only one x-ray image, it is possible to use an average position based on a series of x-ray images. For example, if the tracked path is a circle, the center point of the circle can be used. The relative position of the three-dimensional anatomical image may be known a priori. This relative position of the three-dimensional image may also be determined (or corrected) by registering the three-dimensional anatomical images to the x-ray images using registration techniques known in the art.

The graphical unit 132 creates a composite image comprising a representation of at least part of the three-dimensional anatomical image represented by the dataset 136. This composite image may be stored in a memory (not shown). The graphical unit 132 generates an output signal to be provided to a display 142. The display 142 may be a conventional medical display, such as a high-resolution LCD display, for example, on which 2D projections of the three-dimensional anatomical image represented by the dataset 136 are displayed in conjunction with the indication of the position of the object. The dataset 136 may also comprise one or more two-dimensional images, of which the spatial relation to the object is known, and in such a case the image provided by the graphical unit 132 to the display 142 may comprise such a two-dimensional image with the indication of the object. The display 142 may also be a 3D display, which is a display capable of rendering a three-dimensional impression of a scene. A 3D display can be used to clearly visualize the depth of the object in relation to the three-dimensional anatomical image represented by the dataset 136. Such 3D displays, for example lenticular displays, are known in the art. These visualizations may make manipulations of instruments and/or catheters in tortuous vessels or spaces like atria much easier.

FIG. 2A illustrates a method of estimating the depth parameter of an object in a series of x-ray images. The method may be implemented as a computer program product, for example, embedded in an x-ray apparatus. The method is initiated in step 200, for example in response to a user command via a control interface, for example a button on the x-ray machine.

In step 202, the motor 108 is driven to control a movement of a gantry on which an x-ray source and an x-ray detector are mounted, thereby effectuating a wiggling motion of the gantry. An axis connecting the x-ray source and the x-ray detector traces a surface of a cone, wherein the x-ray source and the x-ray detector have a fixed position with respect to the axis. During the wiggling motion of the gantry, in step 204, a series of x-ray images is acquired.

After having acquired the x-ray images, in step 206, an object appearing in the series of x-ray images is detected and tracked to obtain a tracked path. The tracked path represents a plurality of positions at which the object was detected in the series of images. In step 208, using the tracked path, a depth parameter indicative of a position of the object in a direction substantially parallel to the axis is estimated by comparing the tracked path with a base of the cone.

FIG. 2B is a flowchart illustrating processing steps in a computer program product. The computer program product is arranged for estimating a depth parameter using x-ray images as an input. In step 210, estimation of the depth parameter is initiated by a user. In step 212, the program receives a series of x-ray images acquired during a wiggling movement of a gantry on which an x-ray source and an x-ray detector are mounted, wherein an axis connecting the x-ray source and the x-ray detector traces a surface of a cone, wherein the x-ray source and the x-ray detector have a fixed position with respect to the axis.

In step 214, the program detects and tracks an object appearing in the series of x-ray images to obtain a tracked path, wherein the tracked path represents a plurality of positions at which the object was detected in the series of images. In step 216, the program uses the tracked path for estimating a depth parameter indicative of a position of the object in a direction substantially parallel to the axis by comparing the tracked path with a base of the cone. When the depth parameter has been estimated, the program may compute the three-dimensional position of the object and indicate the position on a display, for example, in an overlay with a three-dimensional image rendering. It is also possible to indicate the position of the object in another x-ray image acquired earlier from a different projection angle.

Figure 3:
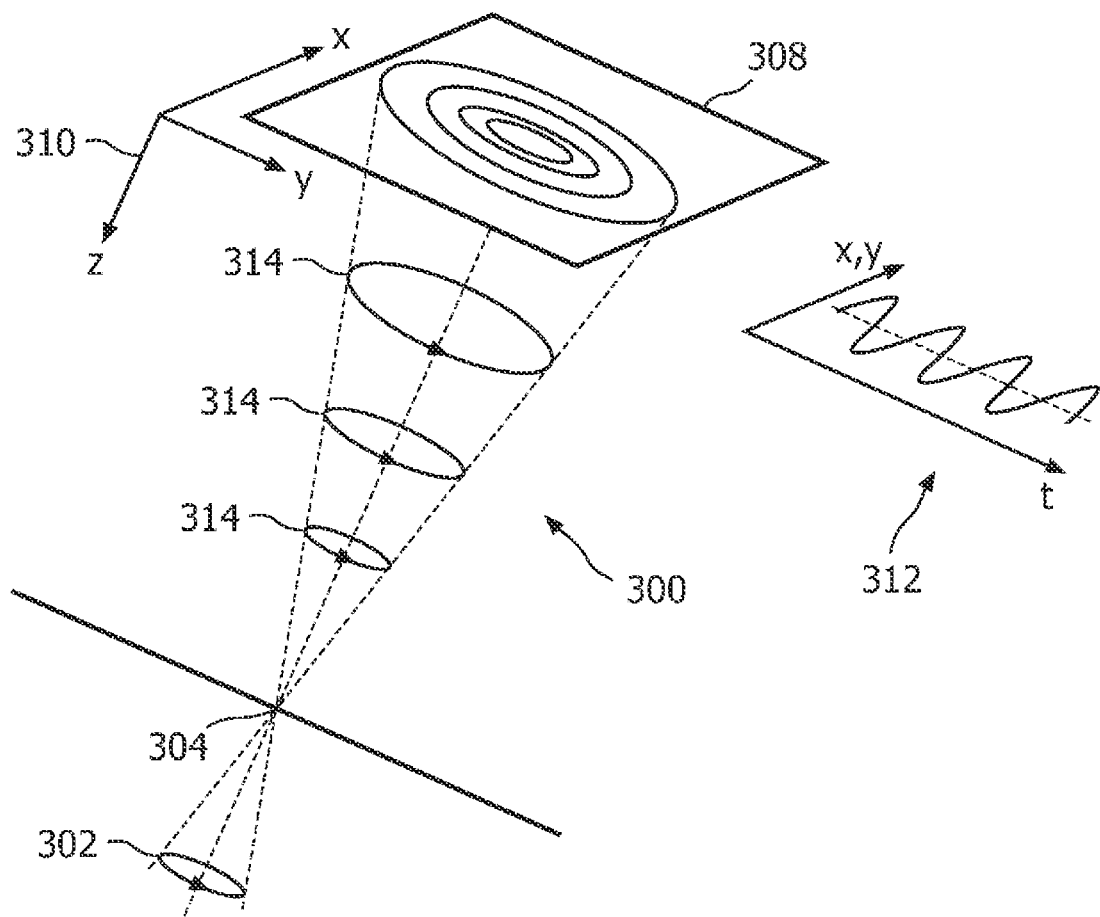
FIG. 3 illustrates schematically a precession of a geometry.

FIG. 3 illustrates schematically a precession movement of an imaging system. Such a precession movement is a particular example of a wiggling movement. The figure illustrates in diagram 300 the trajectory of the source and detector, and in graph 312 the movement of an object as detected by the detector. Circular arrow 302 represents the trajectory of the focal spot of the source. The circular arrows 314 illustrate the movement of an imaginary line connecting the focal spot and the middle point of the detector. Point 304 is the center of precession. It will be understood by the skilled person that an object at the center of precession 304 will remain at a steady position in the images recorded by detector 308 during the precession movement. However, a point at any position that is, compared with the center of precession 304, closer to the detector 308 or closer to the source 302, will appear in the images recorded during the precession as moving in a circle.

The coordinate system 310 is one of the coordinate systems to be used in this document to explain the methods used herein. The x and y axes correspond to the detector plane 308. The z axis is orthogonal to the x,y plane and points to the source 302.

Graph 312 illustrates that a projection of an object not at the center of precession 304 will appear to follow a circular path. When inspecting the position of the object in the detector plane along either axis x or y as a function of time t, a sine-like curve will appear accordingly, as shown in the graph 312.

In the methods and algorithms for depth estimation used herein, an ideal point source and a point object may be assumed. For example, focal blurring may be neglected. A symmetric isocentric situation is described, wherein the center of rotation is approximately half way through the C-arc. However, these assumptions are just simplifications to make the algorithms simpler to develop. The skilled person will appreciate that the accuracy may be improved by taking more aspects such as the ones identified above in consideration in a depth estimation model.

Figure 4A:
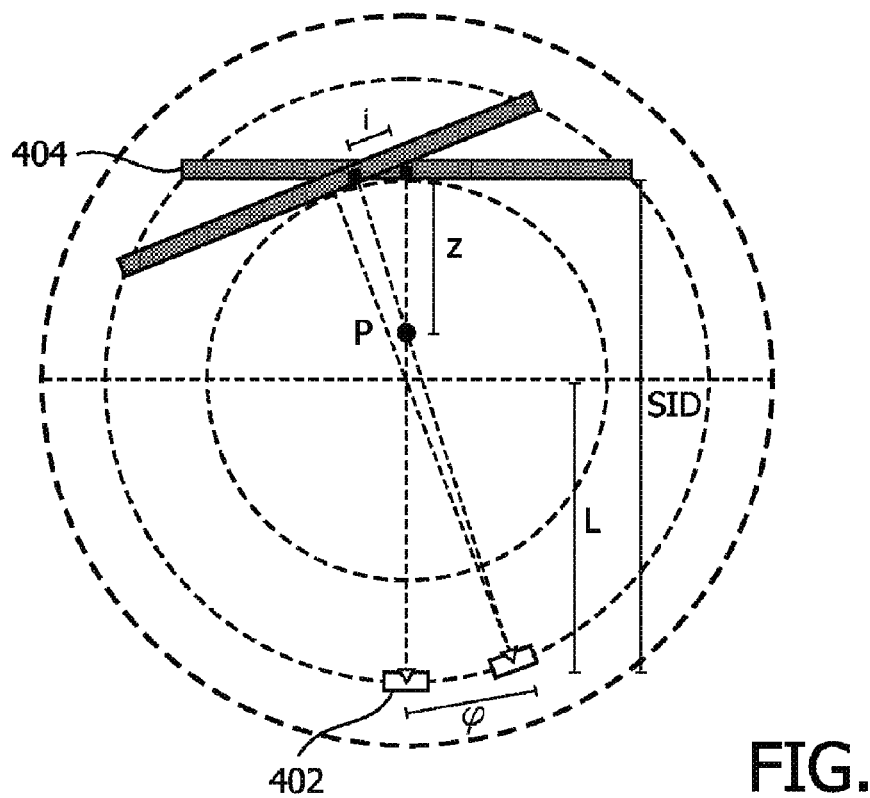
FIGS. 4A and 4B illustrate an approach to depth estimation.
Figure 4B:
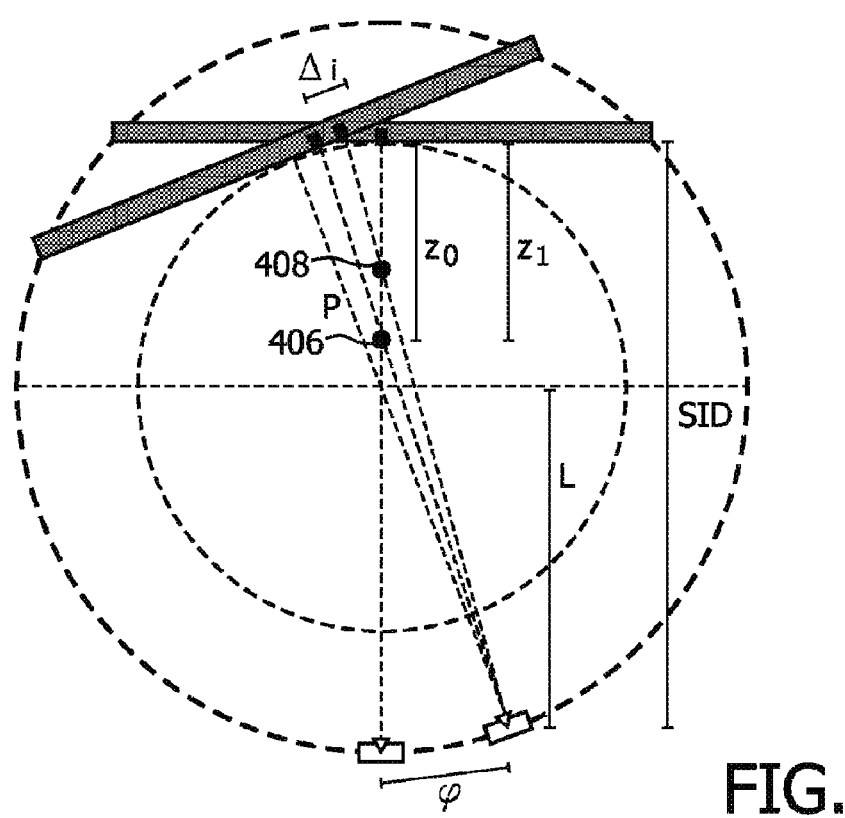

FIGS. 4A and 4B illustrate a parameterized model of a precession. The conventions and symbols used in the model are described in more detail in Table 1.

TABLE 1

List of symbols

| Symbol | Meaning |
|--------|---------|
| P | Point object |
| i | Pixel shift on imager by precession |
| z | Distance from point object to detector |
| SID | Source-imager distance |
| L | Distance from source to center of precession |
| φ | Angle of rotation |

FIG. 4A illustrates an absolute shift in the x,y-plane of a point object when the source 402 and detector 404 are rotated and/or angulated. FIG. 4B illustrates the difference in shift in the x,y-plane for two objects 406 and 408 having a different depth, i.e., two objects having a different z-coordinate. This also illustrates the depth sensitivity of the model. Pixel shift i of a projection of point P in the center of the precession at a distance z from the imaging plane induced by a focal rotation of angle φ may be expressed by:

$$i = \frac{SID \cdot \sin\varphi}{\cos\varphi + \frac{L}{SID - L - z}} \quad \text{Equation 1}$$

Defining $$K = \frac{L}{SID - L - z} \quad \text{Equation 2}$$

and taking into account that angle φ may be relatively small, Equation 1 reduces to:

$$i = \frac{SID}{(1+K)}\varphi \quad \text{Equation 3}$$

Although FIGS. 4A and 4B can be used to analytically calculate depth sensitivity for the model at depth d, a more straightforward approach may be to use a Taylor expansion as an approximation. Differentiating Equation 3 and using a first order Taylor approximation results in:

$$\varphi \approx -\frac{L \cdot (1 + K^2)}{K^2 \cdot SID} \frac{\Delta i}{\Delta z} \quad \text{Equation 4}$$

For a practical situation it may hold that K>>1 and SID approximately equals L. In such a case, for a relatively rough estimation, Equation 4 can be simplified even further to:

$$\varphi \approx -\frac{\Delta i}{\Delta z} \quad \text{Equation 5}$$

where φ is expressed in radians.

According to a model provided by the International Electrotechnical Commission (IEC), a typical value of a patient thickness is 30 cm, where the SID (x-ray source to imager (e.g. x-ray detector) distance) is 1.0 m. In practice, to minimize X-ray dose and focal blurring, the detector is placed close to the patient, for example the PID (patient imager distance) may be roughly 0.15 m. For the current generation of detectors, pixel spacing may be about 150 μm. L may be typically 0.8 m. In such a configuration, a change of the depth parameter of 1 mm would, when using a precession of about 10 degrees, result in a change of the tracked path on the detector of 1 pixel (for example, if the tracked path comprises a circle, the circle's diameter could increase or decrease with 1 pixel).

Figure 5:
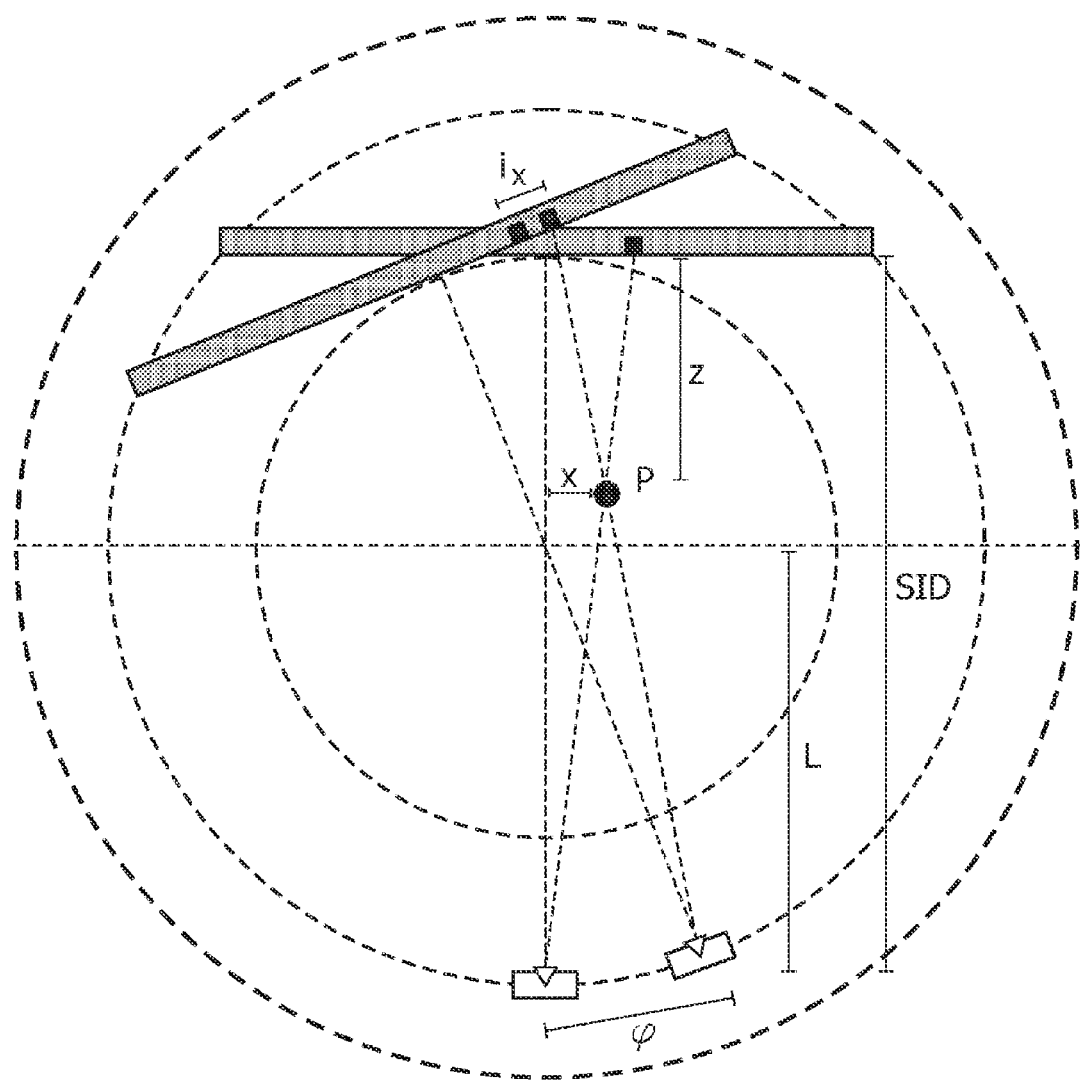
FIG. 5 illustrates an approach to depth estimation of an object having a non-centerline position.
Figure 6A:
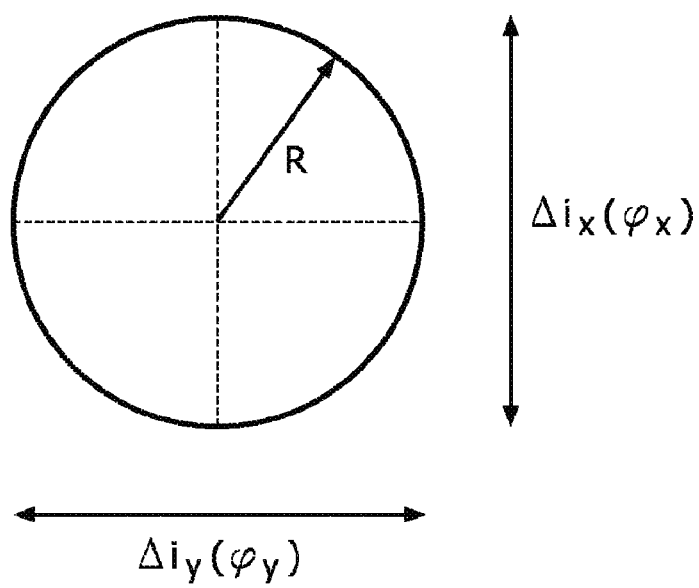
FIGS. 6A and 6B illustrate further aspects of an approach to depth estimation of an object having a non-centerline position
Figure 6B:
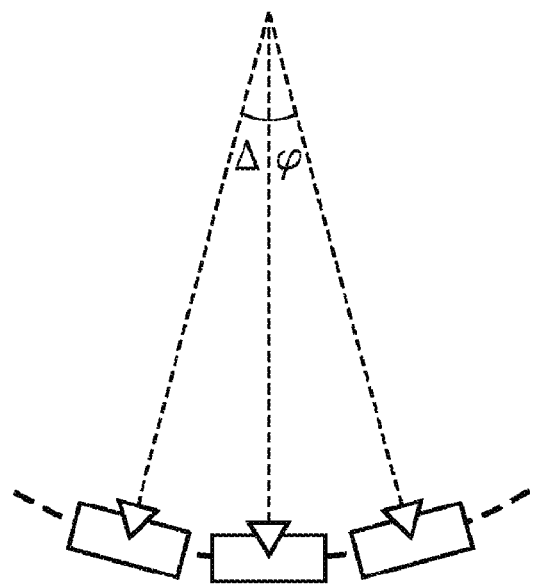

A more comprehensive approach to parameterize depth information by a precession motion is to include a non-centerline position of object P in the model. Herein, the centerline is an imaginary line that is perpendicular to the detector plane and connects the detector and the focal spot of the source. The generalized situation is depicted in FIG. 5 and FIG. 6 where point P is shifted in the x direction. FIG. 5 illustrates the system from the same perspective as FIG. 4A and FIG. 4B. The circle drawn in FIG. 6A illustrates a tracked path of an object projected on the image detector. FIG. 6B illustrates an angle Δφ between two gantry positions. In this description, the situation of a shift in the x-direction will be explained in most detail. In practice, P may shift not only in x-direction (as illustrated in FIG. 5 and FIG. 6), but also in y direction. However, the skilled person may derive similar analysis in case of a shift in y direction, possibly in combination with shift in x direction.

The model is described by:

$$i_x = \frac{(z + L - SID)\sin\varphi - x\cos\varphi}{(z + L - SID)\cos\varphi + x\sin\varphi - L} \cdot SID \quad \text{Equation 6}$$

which would be, due to symmetry, identical for the y-coordinate. From Equation 6 the transfer function for detector pixel shift (which is illustrated in FIG. 6A) at a fixed depth z and as function of position x for a symmetric rotation (precession) may be expressed by:

$$\Delta i_x = \Delta \varphi_x \frac{(x^2 + (z + L - SID)(z - SID))}{(z - SID)^2} \quad \text{Equation 7}$$

where it is assumed that the angle $\Delta\varphi_x$ is relatively small (as illustrated in FIG. 6B) and symmetric with respect to a fixed center of precession 304.

For a precession where the rotation is symmetric (using a dual-axis cone-like trajectory, wherein dual-axis means that rotations of the gantry occur around both the head-to-feet patient axis and the left-to-right patient axis) the radius of a circular trajectory of the projection of the object onto the image plane, modulated by the precession frequency may be given by:

$$R = \frac{1}{2}\sqrt{2}\sqrt{i_x^2 + i_y^2} \quad \text{Equation 8}$$

At a fixed rotational position of the source and detector, the depth sensitivity in the x-direction (and similar in the y-direction) for small angles may be expressed by:

$$\Delta i_x = \frac{SID(x - L \cdot \varphi_x)}{(\varphi_x \cdot x + z - SID)^2} \Delta z. \quad \text{Equation 9}$$

For EP applications, catheters are generally equipped with pairs of electrodes (bipolar) which are relatively easy to detect and track in X-ray images by automatic image processing. This detecting and tracking is facilitated by the blob-like structure on the imager after X-ray projection and the high attenuation of the electrodes. Electrodes are often approximately cylinder shaped and their size is typically 1 mm (perpendicular projection). However, the methods and systems described herein are not limited to electrodes and are also not limited to objects having the dimensions of electrodes.

Table 2 defines a sequence of rotation and angulation values that belong to a precession movement of an X-ray gantry to which an X-ray source and an X-ray detector are fixed. Herein, rotation refers to a rotation of the gantry around an axis in the patient's head-to-feet direction, whereas angulation refers to a rotation of the gantry around an axis in the patient's left-to-right direction.

TABLE 2

Sequential rotation/angulation values of an example trajectory

| Position | Rotation | Angulation |
|----------|----------|------------|
| 1 | 5 | 0 |
| 2 | 5 | 2 |
| 3 | 3 | 4 |
| 4 | 2 | 5 |
| 5 | −1 | 5 |
| 6 | −3 | 4 |
| 7 | −4 | 3 |
| 8 | −5 | 1 |
| 9 | −5 | −1 |
| 10 | −4 | −3 |
| 11 | −3 | −4 |
| 12 | −1 | −5 |
| 13 | 2 | −5 |
| 14 | 3 | −4 |
| 15 | 5 | −2 |

The precession defined in Table 2 is a precession of ±5 degrees, making the maximum angle between any two gantry positions 10 degrees. This angle is based on the estimations from the model of the previous section. Rotation and angulation describe a trajectory along a circle with a radius of 5 degrees (precession). The angles listed in Table 2 are with respect to a reference position in the center of the precession (the axis around which the precession performs a rotating movement). This reference position can have any orientation (i.e., any pair of absolute angulation/rotation values). Typically the reference position will follow from the clinical procedure and from the patient's anatomy. The values in this example are for illustration only. They are not limitations in any way.

The positions of the objects in the images may be identified either manually, semi-automatically, or preferably fully automatically. For example, lead or metallic objects may be identified automatically by thresholding the image, thereby segmenting dark areas corresponding to the objects, followed by a blob detection algorithm which determines the center positions of the dark areas in the image sequence. These center positions may be used as the x,y coordinates of the objects in the images.

As described above, the radius of the (circular) trajectory traversed by the projection of an object in the image sequence is proportional to the depth position of the projected object. The rotation direction of the trajectory (clockwise or counter clockwise) is related to the position of the object relative to the isocenter.

Since the precession motion modulates the trajectory of the object as recorded in the image sequence with a predefined frequency, dedicated signal processing can be employed to determine the depth position of a tracked object in more difficult imaging situations, for example if there is much noise in the image or if there are other objects in the image which might be erroneously mistaken for the object whose depth is to be determined. The shape of the predefined trajectory can also be advantageously be taken into account where object motion plays a role, for example gastrointestinal motion, cardiac motion, and/or respiratory motion.

The object may not be static. For example, the object may move due to cardiac and respiratory motion, as well as gastrointestinal motion. The depth estimation may be improved by means of a motion model which models the motion of the object based on the image sequence. This may be done using a filter that estimates the state of a dynamic system from a series of incomplete and noisy measurements. Such a motion model may provide accurate continuously-updated information about the position and velocity of an object based on a sequence of observations about its position. Such a sequence of observations is provided by the image sequence and the sequence of positions at which the object was detected in the images. An example filter that may be applied to design such a motion model is the known Kalman filter, which is a linear system in which the mean squared error between the desired output and the actual output is minimized when the input is a random signal generated by white noise.

When applying the method to patients who are suffering from atrial fibrillation, the object to be localized (typically one or more EP-catheters which are inserted in a heart chamber) may not move as much as in a regularly beating heart. This enables the use of the depth estimation system with no motion compensation or only little motion compensation. In this situation it may be especially advantageous to use the systems and methods described herein, because in the situation of atrial fibrillation it may be difficult to find a facility having dedicated navigation equipment and/or it may be too time-consuming to setup such dedicated navigation equipment in time.

With a precession of 10 degrees (radius of ±5 degrees) the absolute displacement of the detector may be roughly 5 cm in a common X-ray system. Although detector motion for this situation is relatively small, it may still be somewhat uncomfortable for the patient and/or the physician. The precession angle may be decreased to reduce any discomfort caused by the precession. By increasing the precession angle, depth resolution may increase proportionally. However, the accuracy of some of the existing electromagnetic tracking systems is in the same order of magnitude, typically 2-4 mm for EP catheters.

The radius of the trajectory of the tracked object may be proportional to the distance of the object to the detector and is zero if the object is located in the isocenter of the geometry. However, as can be concluded from the model, the depth sensitivity is virtually independent of the actual depth position of the object.

Figure 7:
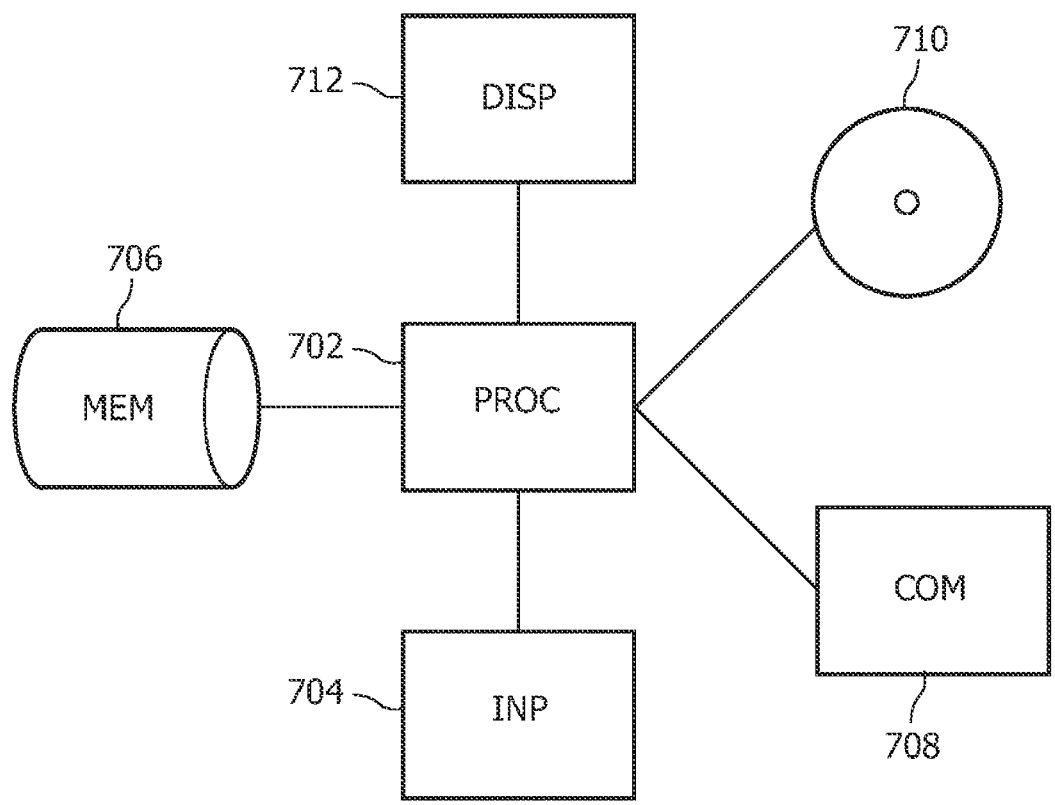
FIG. 7 is a diagram of an architecture of an embodiment.

FIG. 7 illustrates a system architecture suitable for creating a computer implementation of aspects of the methods and systems described herein. Such an architecture may be found in a computer workstation, for example. Alternatively, the components shown in FIG. 7 may be incorporated in an x-ray system. FIG. 7 shows only a schematic of an example architecture. Other architectures may be used instead. A memory 706 comprises computer instructions according to a method described in this text. The memory 706 may also comprise image data and object location data. Processor 702 executes the computer instructions. Communication port 708 is used to receive image data, for example a dataset 136 representing a three-dimensional anatomical object and/or an image sequence 134. The port 708 may also be used to dispatch control signals to a motor 108 of a gantry 102. The image data may also be obtained via a removable media 710. User commands may be input via input 704 (e.g., keyboard or tableside control), to trigger certain actions such as initiating a wiggling motion and/or initiating display of an indication of a three-dimensional position of an object with respect to a three-dimensional anatomical image. The display 712 may be used to show status information and/or the indication of the object and image. It will be apparent to the skilled person how to connect the architecture of FIG. 7 via the communication port 708 to an x-ray system, or how to embed the architecture into a known x-ray system.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An x-ray system comprising
a gantry on which an x-ray source and an x-ray detector are mounted;
at least one motor for rotating the gantry;
a control unit for controlling the x-ray source and the x-ray detector to acquire x-ray images and for driving the motor to control a movement of the gantry, wherein the control unit comprises means for effectuating a wiggling motion of the gantry, wherein an axis connecting the x-ray source and the x-ray detector traces a surface of a cone, wherein the x-ray source and the x-ray detector have a fixed position with respect to the axis, wherein the control unit comprises means for acquiring a series of x-ray images during the wiggling motion of the gantry;
an object recognition unit for detecting and tracking an object appearing in the series of x-ray images to obtain a tracked path, wherein the tracked path represents a plurality of positions at which the object was detected in the series of images; and
a depth estimation unit for using the tracked path for estimating a depth parameter indicative of a position of the object in a direction substantially parallel to the axis.

2. The x-ray system according to claim 1, wherein the wiggling motion spans an angle of at most about 10 degrees, wherein the angle is measured with respect to the axis.

3. The x-ray system according to claim 1, wherein a displacement of the x-ray source during the wiggling motion is not greater than a dimension of the x-ray detector.

4. The x-ray system according to claim 1, wherein the wiggling motion is a periodic motion.

5. The x-ray system according to claim 1, wherein the cone has a circular base or an elliptical base.

6. The x-ray system according to claim 1, wherein the cone has a linearly shaped base.

7. The x-ray system according to claim 1, wherein the depth estimation unit comprises
means for comparing a base of the cone with the tracked path, thereby obtaining a scale of the tracked path; and
means for estimating the depth parameter based on the scale of the tracked path.

8. The x-ray system according to claim 7, wherein the base of the cone comprises a circle, wherein the tracked path defines a circle, and the scale of the tracked path is based on a radius of the circle defined by the tracked path.

9. The x-ray system according to claim 1, wherein the depth estimation unit comprises a motion model for discriminating the movement of the gantry and a movement of the object.

10. The x-ray system according to claim 1, wherein the object comprises at least a tip or an electrode of an electrophysiology ablation catheter.

11. The x-ray system according to claim 1, wherein the x-ray system is arranged for performing the wiggling motion while imaging a human patient during a percutaneous intervention.

12. The x-ray system according to claim 1, further comprising a graphical unit for indicating a position of the object with respect to a three-dimensional anatomical image represented by a dataset, based on the depth parameter and based on a position of the object in an x-ray image.

13. The x-ray system according to claim 12, further comprising a display for providing a three-dimensional graphical representation of the three-dimensional anatomical image and the position of the object, wherein the graphical unit is arranged for providing a signal representing the indication to the display.

14. A method comprising
driving a motor to control a movement of a gantry on which an x-ray source and an x-ray detector are mounted, thereby effectuating a wiggling motion of the gantry, wherein an axis connecting the x-ray source and the x-ray detector traces a surface of a cone, wherein the x-ray source and the x-ray detector have a fixed position with respect to the axis;
acquiring a series of x-ray images during the wiggling motion of the gantry;
detecting and tracking an object appearing in the series of x-ray images to obtain a tracked path, wherein the tracked path represents a plurality of positions at which the object was detected in the series of images; and
using the tracked path for estimating a depth parameter indicative of a position of the object in a direction substantially parallel to the axis by comparing the tracked path with a base of the cone.

15. A computer program product comprising a non-transitory computer readable medium embodying machine readable instructions for causing a machine to perform the steps:
receiving a series of x-ray images acquired during a wiggling movement of a gantry on which an x-ray source and an x-ray detector are mounted, wherein an axis connecting the x-ray source and the x-ray detector traces a surface of a cone, wherein the x-ray source and the x-ray detector have a fixed position with respect to the axis;

detecting and tracking an object appearing in the series of x-ray images to obtain a tracked path, wherein the tracked path represents a plurality of positions at which the object was detected in the series of images; and using the tracked path for estimating a depth parameter indicative of a position of the object in a direction substantially parallel to the axis by comparing the tracked path with a base of the cone.

* * * * *